US007172775B2

(12) United States Patent
Petersen et al.

(10) Patent No.: US 7,172,775 B2
(45) Date of Patent: Feb. 6, 2007

(54) METHOD FOR PREPARING BREWERS WORT

(75) Inventors: Erin Ellice Petersen, London (CA); Argyrios Margaritis, London (CA); Robert Joseph Stewart, London (CA); Phyllis Heather Pilkington, London (CA); Michael J. McGarrity, London (CA); Normand Anthony Mensour, Ancaster (CA); Clemens Forster, London (CA); Jadwiga A. Sobczak, London (CA)

(73) Assignee: Labatt Brewing Company Limited, London (CA)

( * ) Notice: Subject to any disclaimer, the term of this patent is extended or adjusted under 35 U.S.C. 154(b) by 451 days.

(21) Appl. No.: 10/270,240

(22) Filed: Oct. 15, 2002

(65) Prior Publication Data

US 2003/0087000 A1     May 8, 2003

Related U.S. Application Data

(60) Provisional application No. 60/328,448, filed on Oct. 12, 2001.

(51) Int. Cl.
*C12C 7/00* (2006.01)
*C12C 11/00* (2006.01)

(52) U.S. Cl. ........................................ 426/16
(58) Field of Classification Search ................ 426/11, 426/15, 16
See application file for complete search history.

(56) References Cited

U.S. PATENT DOCUMENTS 4,790,238 A * 12/1988 Hsu ............................ 99/276

OTHER PUBLICATIONS

The Encyclopedia of Beer, 1995, Henry Holt and Company, Inc., First Edition, p. 201.*
Baker et al, Rapid Beer Production and Conditioning Using a Plug Fermentation J. Inst. Brewing, vol. 79, pp. 487-494 (1973).
Dulieu et al., Improved Performances and Control of Beer Fermentation using Encapsulated α-Acetolactate Decarboxylase and Modeling, Biotechnol. Prog. vol. 16, pp. 958-965 (2000).
Gjermansen et al., Construction of a Hybrid Brewing Strain of Saccharomyces Carlsbergensis by Mating of Meiotic Segregants, Carlsberg Res. Commun., vol. 46, pp. 1-11, (1981).
Godtfredsen et al., Use of α-Acetolactate Decarboxylase for Accelerated Maturation of Beer, EBC Congress, Lecture No. 17, pp. 161-168, (1983).
Godtfredsen et al., The Occurrence of α-Acetolactate Decarboxylases Amoung Microorganisms, Carlsberg Res. Commun., vol. 48, pp. 239-247, (1983).
Haukeli et al., Conversion of α-Acetolactate and Removal of Diacetyl a Kinetic Study, J. Inst. Brew., vol. 84, pp. 85-89, (1978).
Inoue et al, Mechanism of Diacetyl Formation in Beer, Proceedings of the American Society of Brewing Chemists, vol. 26, pp. 158-165 (1968).
Inoue et al., Diacetyl and Beer Fermentation, Proceedings of the American Society of Brewing Chemists, vol. 28, pp. 198-208, (1970).
Inoue et al., Formation of Acetohydroxy Acids During Uptake of Amino Acids by Yeasts, Proc. American Soc. Brew. Chem., vol. 31, pp. 36-39, (1973).
Inoue, The Relationship between the Performance of Yeast and Acetohydroxy Acid Formation during Wort Fermentation, MBAA Technical Quarterly, vol. 17, pp. 62-65, (1981).
Inoue et al., Direct Spontaneous Conversion of Acetolactate into Non-Diacetyl Substance in Fermenting Wort, Eur. Brew. Conv. Proc. Cong., pp. 369-376, (1991).
Jones et al., Absorption of Amino Acids from Wort by Yeasts, J. Inst. Brew., vol. 70, pp. 307-315, (1964).
Jones et al., Nitrogen Requirements in Wort-Practical Applications, Euro. Brew. Conv. Proc., 12th Congress, pp. 151-160, (1969).
Jones et al., Regulation of Amino Acid and Nucleotide Biosynthesis in Yeast, Cold Spring Harbor Laboratory, pp. 181-299, (1982).
Maule et al., Simultaneous Assessment of Changes Occurring During Batch Fermentation, J. Inst. Brew., vol. 72, pp. 488-494, (1966).
Mithieux et al., Tandem Integration of Multiple ILV5 Copies and Elevated Transcription in Polyploid Yeast, University of Sydney, vol. 11, pp. 311-316, (1995).
Nakatani et al, Kinetic Study of Vicinal Diketones in Brewing (I) Formation of Total Vicinal Diketones, MBAA Technical Quarterly, vol. 21, pp. 73-78, (1984).
Nakatani et al., Kinetic Study of Vicinal Diketones in Brewing, II: Theoretical Aspect for the Formation of Total Vicinal Diketones, MBAA Technical Quarterly, vol. 21, pp. 175-183, (1984).
Onaka et al., Beer Brewing with Immobilized Yeast, Bio/Technology, vol. 3, pp. 467-470, (1985).
Owades et al., Nitrogen Metabolism during Fermentation in the Brewing Process. II. Mechanism of Diacetyl Formation, Amer. Soc. Brew. Chem., vol. 17, pp. 22-26, (1959).
Palmqvist et al., Uptake of Amino Acids in Bottom Fermentations, Int. Brew., vol. 75, pp. 181-190, (1969).
Portno et al., Some Factors Affecting the Concentration of Diacetyl in Beer, J. Inst. Brew., vol. 72, pp. 193-196, (1966).

(Continued)

*Primary Examiner*—Arthur L. Corbin
(74) *Attorney, Agent, or Firm*—Levy & Grandinetti (57) ABSTRACT

A method for predicting late fermentation production of diacetyl in a brewing process comprises determining the ratio of FAN (free amino nitrogen content) to sugar (fermentable) to specific gravity in an initial wort composition. In addition there is provided a process for preventing incipient late fermentation production of diacetyl in a brewing process, comprising measuring and variously adjusting the initial FAN, sugar and specific gravity of the wort such that the ratio $$\frac{[f \cdot \text{sugar}(g/L)]_{initial}}{[\text{FAN}(g/L)]_{initial}[\text{Gravity}(°P)]_{initial}},$$

for the adjusted wort has a value of 37 or less.

5 Claims, 9 Drawing Sheets

OTHER PUBLICATIONS

Scherrer, Formation and Analysis of Diacetyl, 2,3-Pentanedione, Acetoin and 2,3-Butanediol in Wort and Beer, Wallerstein Lab. Comm., vol. 35, pp. 5-33, (1972).

Satyanarayana et al., Biosynthesis of Branched-Chain Amino Acids in Yeast: Regulation of Leucine Biosynthesis in Phototrophic and Leucine Auxotrophic Strains, Jour. of Bacteriology, vol. 96, pp. 2018-2023, (1968).

Suihko et al, Pilot-Brewing with α-Acetolactate Decarboxylase Active Yeasts, J. Euro. Brew. Conv. Proc. Congr. Zurich, pp. 483-490, (1989).

Takahashi et al., Genetic Modification of Brewer's Yeast to Produce Acetolactate Decarboxylase and the Safety Aspects of the Beer Brewed by the Transformed Yeast, Amer. Chem. Soc., vol. 605, pp. 171-180, (1995).

Villa et al., Control of Vicinal Diketone Production by Brewer's Yeast. I. Effects of ILV5 and ILV3 Gene Amplification on Vicinal Diketone Production and ILV Enzyme Activity, Amer. Soc. Brew. Chem., vol. 53, pp. 49-53, (1995).

Villanueba et al., Subthreshold Vicinal Diketone Levels in Lager Brewing Yeast Fermentations by Means ILV5 Gene Amplification, Amer. Soc. of Brew. Chem., vol. 48, pp. 111-114, (1990).

Yamano et al., Brewing Performance of a Brewer's Yeast Having α-Acetolactate Decarboxylase from Acetobacter Aceti Subsp. Xylinum, Elsevier Science B.V., vol. 39, pp. 21-26, (1995).

Yamauchi et al., Rapid Maturation of Beer using an Immobilized Yeast Bioreactor. 1. Heat Conversion of Alpha-Acetolactate, Journal of Biotechnology, vol. 38(2), pp. 109-115, (1995).

Yamauchi et al., Rapid Fermentation of Beer Using an Immobilized Yeast Multistage Bioreactor System, Biochemistry and Biotechnology, vol. 53, pp. 261-276, (1995).

Yoshida et al., Malt Quality and Amino Acid Composition of Wort, Part I. The Absorption of Free Amino Acids by Bottom-Fermenting Yeast During Primary Fermentation, Rept. Res. Lab. Kirin Brewery Co., No. 11, pp. 63-75, (1968).

Yoshida, Malt Quality and Amino Acid Composition of Wort, Part II. Relation of Qualitative and Quantitative Contents of Free Amino Acids in Wort to Its Fermentability, Rept. Res. Lab. Kirin Brewery Co., No. 11, pp. 77-86, (1968).

* cited by examiner

MEDIUM PREPARATION

| Initial Wort Characteristics-Typical Lager Wort | | | | | | | | |
|---|---|---|---|---|---|---|---|---|
| sp.gr. (deg P) | [FAN]$_{int}$ (g/L) | [F.Sug]$_{int}$ (g/L) | [fsug]$_{int}$/[FAN]$_{int}$ (g/g) | Cell$_{int}$ g/L (wet) | mg$_{O2}$/L deg P (mg/L.P) | [F.Sug]$_{int}$/Plato.[FAN]$_{int}$ (g/g.P) | [Valine]$_{int}$ (mg/L) | Diacetyl Double Peaks |
| LCC# 3290 Trial 1 | | | | | | | | |
| 16.71 | 0.257 | 122.1 | 475.1 | 3.3 | 1.0 | 28.4 | 211.0 | no |
| 14.23 | 0.230 | 104.0 | 452.2 | 2.8 | 1.0 | 31.8 | 181.0 | no |
| 12.01 | 0.215 | 86.7 | 403.3 | 2.4 | 1.0 | 33.6 | 146.0 | no |

Figure 12

| Initial Wort Characteristics-Supplemented Lager Wort | | | | | | | | |
|---|---|---|---|---|---|---|---|---|
| sp.gr. (deg P) | [FAN]$_{int}$ (g/L) | [F.Sug]$_{int}$ (g/L) | [fsug]$_{int}$/[FAN]$_{int}$ (g/g) | Cell$_{int}$ g/L (wet) | mg$_{O2}$/L deg P (mg/L.P) | [F.Sug]$_{int}$/Plato.[FAN]$_{int}$ (g/g.P) | [Valine]$_{int}$ (mg/L) | Diacetyl Double Peaks |
| LCC# 3290 Trial 1 | | | | | | | | |
| 21.17 | 0.252 | 166.2 | 659.5 | 4.3 | 1.0 | 31.2 | 150.0 | no |
| 17.53 | 0.213 | 139.6 | 655.4 | 3.5 | 1.0 | 37.4 | 130.0 | yes |
| 12.72 | 0.153 | 92.7 | 605.9 | 2.6 | 1.0 | 47.6 | 112.0 | yes |
| LCC# 3290 Trial 2 | | | | | | | | |
| 21.34 | 0.254 | 171.0 | 673.2 | 4.3 | 1.0 | 31.5 | 147.0 | no |
| 17.44 | 0.204 | 137.7 | 675.0 | 3.5 | 1.0 | 38.7 | 131.0 | yes |
| 13.54 | 0.162 | 103.9 | 641.4 | 2.7 | 1.0 | 47.4 | 115.0 | yes |
| LCC# 3290 Trial 3 | | | | | | | | |
| 21.23 | 0.260 | 186.4 | 716.9 | 4.2 | 1.0 | 33.8 | 142.0 | no |
| 17.03 | 0.189 | 145.7 | 770.9 | 3.4 | 1.0 | 45.3 | 107.0 | yes |
| 13.52 | 0.150 | 114.4 | 762.7 | 2.7 | 1.0 | 56.4 | 83.0 | yes |

METHOD FOR PREPARING BREWERS WORT

We claim the benefit Under Title 35, United States Code, §120 to U.S. Provisional Application No. 60/328,448, filed Oct. 12, 2001, entitled THE EFFECT OF FERMENTATION MEDIA COMPOSITION ON VICINAL DIKETONE EVOLUTION.

FIELD OF THE INVENTION

The invention relates to the preparation of brewers wort, and more specifically, to the preparation thereof for use in batch fermentations in which late diacetyl formation is controlled as a function of initial wort constitution.

BACKGROUND OF THE INVENTION

The dynamics of yeast fermentation is of fundamental importance to the success of the brewing process. Hundreds, if not thousands of biochemical reactions transform the wort into the finished beer and through their various interactive combinations and permutations have a cumulative impact on flavor, ethanol content, productivity, colour, aroma, body and foam stability. In the end, these figure largely as determinants of the ultimate quality/cost of the product, and in turn, the consumer demand for it. Over 1,000 compounds have been identified in beer which contribute to its flavor— and each is variously effected by availability of metabolites and processing conditions.

Over the course of typical batch fermentation processes a number of general changes occur. Fermentable sugars are consumed, and unfermentable sugars are converted, and then consumed, all in a more or less orderly sequencing that is related to corresponding ease with which the yeast is able to convert these respective carbohydrate materials into useful energy. The pH of the wort decreases. The yeast cell population goes through a lag phase, then a log phase and finally a stationary phase, before falling into decline.

In addition to the changes listed above, there is a more or less sequential, and generally ordered uptake of amino acids from the wort, (by the yeast), via a complex transport system that is mediated by specific and general permeases. As fermentation progresses, there are large and corresponding fluctuations in the types and concentrations of amino acids that remain usefully available to the yeast population. More specifically, amino acids are classified according to their respective "uptake" characteristics, such as: initial starting time; duration of uptake; and, speed of uptake after inoculation of the medium with yeast (Jones and Pierce, 1964, 1969; Maule et al., 1966; Nakatani et al., 1984 b; Palmqv and Ayrapaa, 1969; Yoshida et al., 1968 a,b). According to this typology, four main groups of amino acids have been defined. Type 'A' amino acids are absorbed by yeast from the start of fermentation and are essentially removed from the wort within 20–24 hours. Type 'B' amino acids, on the other hand, are taken up after a lag period of 12 hours after which they are rapidly taken up by the yeast. Type 'C' amino acids have a longer lag period than type B's before uptake occurs (about 20 hours) and some can even still remain in the final beer if initial wort concentrations are high enough. Type 'D' amino acids (e.g. proline), are not assimilated by the yeast in nitrogen rich media. According to the prior art the wort composition has some effects on the rate of uptake of the individual amino acids, but that overall, the uptake of amino acids is generally faithful to this ordered pattern of consumption. This sequential uptake of amino acids is believed to be due to a complex system of amino acid permeases, each having a particular specificity for certain amino acid groups.

The above mentioned fluctuations impact on the enzymatic biosynthesis of valine, particularly during classical type 'B' amino acid uptake. This results in cyclical repression/derepression of the metabolic pathways that affect the evolution of extracellular diacetyl. Diacetyl, a vicinal diketone (vicinyl diketone), has a low taste threshold, and imparts a strong buttery/toffee flavor that is considered to be a defect in many beer products.

Diacetyl is, however, a largely incidental by-product of yeast metabolism—and normally serves as an intermediate that is consumed during subsequent fermentation to below perceptual thresholds at some point in time at or near "completion"—or at least after some reasonably brief maturation process. It arises spontaneously (a non-enzymatic oxidation reaction) from precursors in the isoleucine-valine biosynthetic pathway and the need to reduce its concentration to levels below human perceptual thresholds can result in a need for prolonged beer maturation processing, (or other remedial processing), with attendant production costs.

Figure 1:
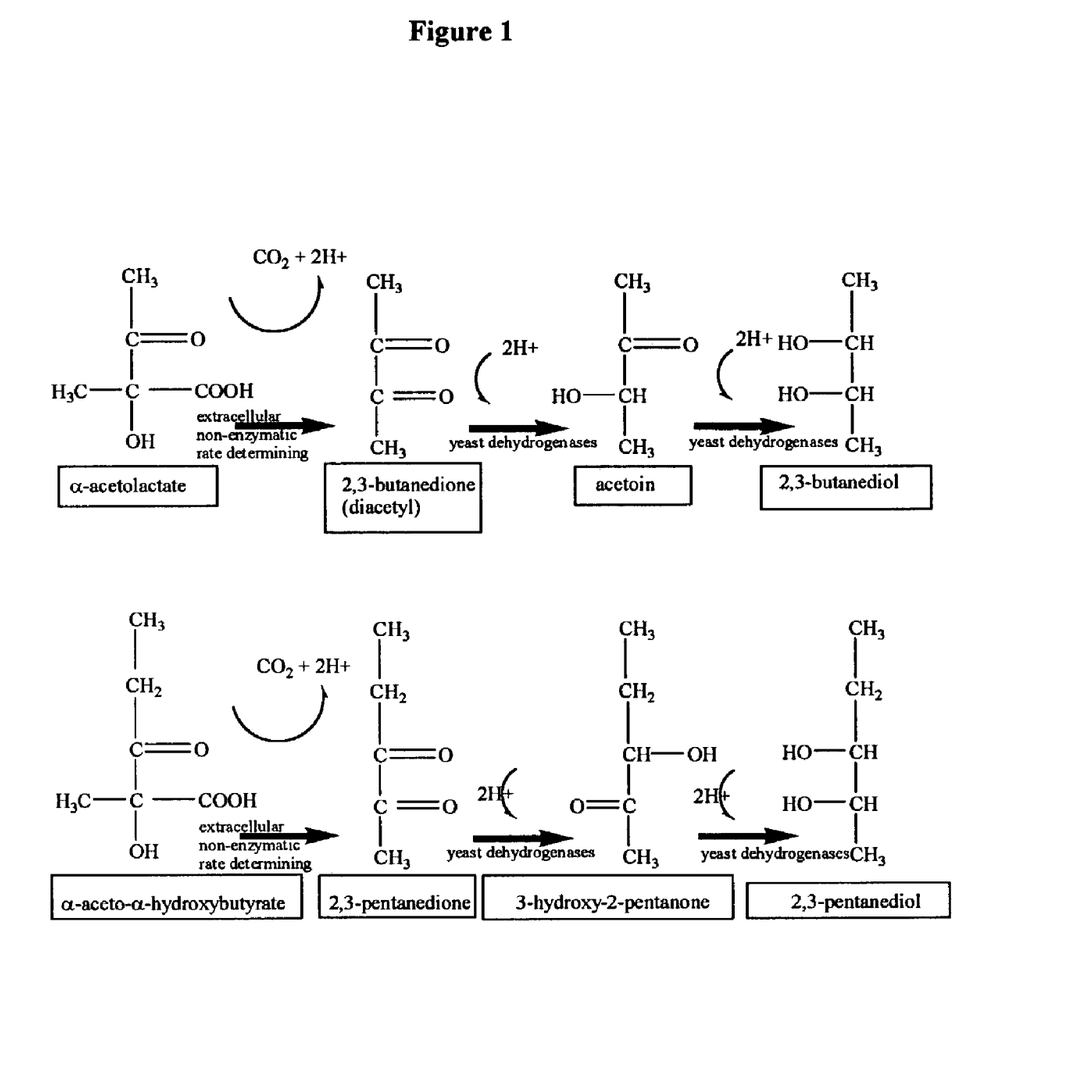
Figure 2:
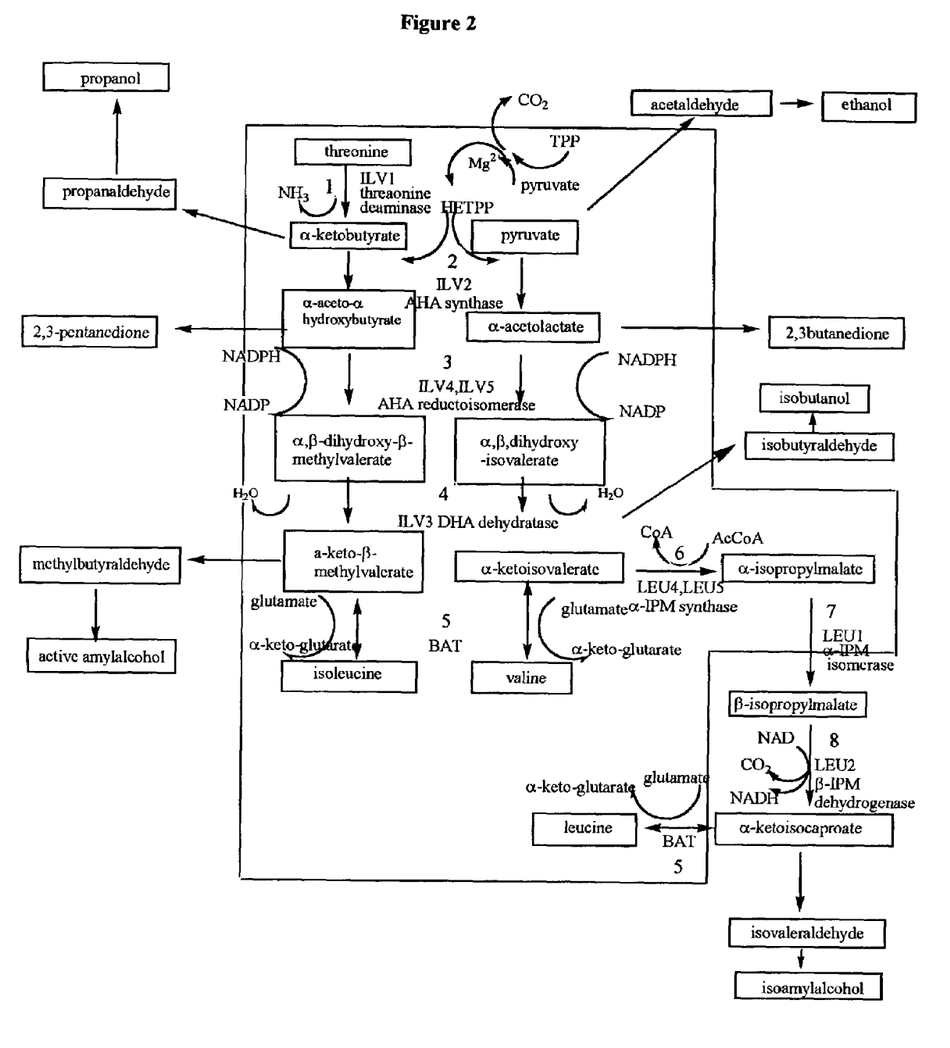

As a result of the aforementioned metabolic dynamics, a first peak in diacetyl concentration normally occurs relatively early in the course of the typical batch fermentation. The diacetyl concentration is subsequently reduced as the yeast takes up diacetyl and converts it enzymatically into acetoin, which in its turn is further metabolized. More specifically, diacetyl is believed to be a by-product of amino acid biosynthesis involving a relationship between amino acid biosynthesis and acetolactate formation, the precursor to diacetyl (Jones and Fink, 1982). Alpha-acetolactate is excreted by the yeast where upon a non-enzymatic oxidative decarboxylation transforms it into diacetyl (Inoue et al., 1968). In parallel to this, in the isoleucine biosynthetic pathway, 2,3-pentanedione is transformed extracellularly from α-aceto-α-hydroxybutyrate, the intermediate, by a similar non-enzymatic decarboxylation reaction. Yeast cells cannot assimilate the extracellular acetohydroxy acids, but they do take up diacetyl and 2,3-pentanedione which undergo enzymatic conversion to acetoin and 3-hydroxy-2-pentanone, respectively. Acetoin is further enzymatically converted to 2,3-butanediol, and 3-hydroxy-2-pentanone to 2,3-pentanediol as seen in FIG. 1. Diacetyl is reduced by the yeast 50 times faster than its rate of formation from α-acetolactate, thus the oxidative decarboxylation step is the rate-determining step (Inoue and Yamamoto, 1970). Diacetyl reduction depends on yeast strain and temperature and decreases gradually in the later stages of fermentation (Haukeli and Lie, 1978).

Problems, however arise when ongoing metabolic fluctuations result in the late fermentation production of diacetyl in amounts that create a second peak in its concentration or otherwise prolongs the presence of an elevated concentration of diacetyl in the wort. The higher diacetyl levels resulting from late fermentation production may not be reduced to below its flavour threshold in a timely manner. The overall concentration of diacetyl in the wort at any given time both during and "post" fermentation, is a combination of the rate of formation of α-acetolactate, its conversion rate, and the rate of reduction of diacetyl to 2,3-butanediol and acetoin. Any latency of elevated diacetyl concentration resulting from late fermentation production thereof, must be reduced before the beer can be further processed—which may necessitate prolonged maturation or other remedial treatments/measures to bring the final diacetyl concentration to within the target specification for the desired end product.

The prior art offers many approaches to the problem of resolving diacetyl issues in beer production.

Amino acids addition has been attempted, in the hope of altering enzymatic regulation of the isoleucine-valine biosynthetic pathway to mitigate diacetyl problems. In general, levels of diacetyl and 2,3-pentanedione throughout the course of fermentation have been found to be related to the initial concentrations of FAN. More specifically, diacetyl and 2,3-pentandione have been effected, in different ways, by different amounts and combinations of the initial concentrations of isoleucine, valine, threonine and leucine in the wort. However, only the addition of valine to wort consistently reduced the amount of diacetyl formed throughout fermentation. No other single or combined supplementation of wort amino acids was shown to have the same effect (Owades et al., 1959; Portno,1966; Maule et al.,1966; Scherrer,1972; Inoue et al.,1973; Nakatani et al., 1984a; Nakatani et al.,1984b). The addition of isoleucine increased diacetyl and or α-acetolactate, but suppressed 2,3-pentanedione (Scherrer (1972; Inoue et al., 1973; Nakatani et al., 1984a; Nakatani et al., 1984b). The addition of threonine gave a small decrease in diacetyl, but increased the amount of 2,3-pentanedione produced (Scherrer, 1972). The relationship between amino acid transport across the membrane and amino acid biosynthesis was demonstrated by Inoue et al. (1973) who showed that there was an inhibition of AHA synthase which reduced the amount of α-acethydroxy acids being produced during the uptake of valine and isoleucine. And on a more practical side, Nakatani et al., 1984a; Nakatani et al., 1984b discuss a minimum FAN level which, if realized, would reduce the maximum amount of vicinyl diketones produced.

Other prior art approaches have focused on wort composition and growth control to reduce diacetyl—based on the showing that high diacetyl may be related to valine exhaustion from the wort before the end of growth (Inoue et al., 1973; Inoue, 1981; Inoue, 1988; Onaka et al., 1985).

Still other prior art offerings include genetic manipulation of the yeast. Efforts to decrease acetolactate synthetase activity were attempted by the Carlsberg group in Denmark (Gjermansen and Sigsgaard, 1987). Much genetic research, making efforts to strengthen the activity of acetolactate reductoisomerase by amplification of the ILV5 region (gene expressing AHA reductoisomerase) has been done (Villanueba, Goossens and Masschelein, 1990; Muthieux and Weiss, 1995; Villa et al., 1995). Work on introducing the acetolactate decarboxylase enzyme from bacteria enables the yeast to convert acetolactate, the precursor of diacetyl, to acetoin directly without affecting other fermentation characteristics (Godtfredsen et al., 1983; Godtfredsen, Lorck and Sigsfaard, 1983; Suihko et al., 1989; Yamano, and Tanaka and Inoue, 1991; Yamano et al., 1995; Takahashi et al. 1995).

The more traditional approach of the brewing industry involves the management of maturation time and/or increased temperature are another method of diacetyl reduction. A heat treatment process during the anaerobic primary fermentation stage can reduce the maturation process as the anaerobic condition allows the conversion of alpha-acetolactate to acetoin directly (Yamauchi et al., 1995a, 1995b; Inoue et al., 1991; Barker and Kirsop, 1973).

Dulieu et al., 1997; 2000, proposed using alpha-acetolactate decarboxylase in an encapsulated fixed bed bioreactor application, to reduce fermentation/maturation time by reducing the amount of alpha-acetolactate that is converted into diacetyl. Notwithstanding the prior art offerings, it would be advantageous to find a way to manage diacetyl formation in beer production that did not require the addition of exogenous enzymes, specialty amino acid addition, genetic manipulation, or complicate processing through energy-expensive heating, or delaying the release of fresh beer in order that protracted holding times would allow the diacetyl to dissipate.

SUMMARY OF THE INVENTION

Broadly speaking, present invention provides an opportunity to control diacetyl production but based on a better fundamental understanding of the effects of wort composition and depletion during fermentation, especially as it relates to amino acid biosynthetic pathways—and in particular in the context of the industrial environment where the yeast physiology/biochemistry of production brewing strains acting on complex industrial media is a reality. A priori predictability of what effects diacetyl production is enormously complicated owing to the nature of brewery wort. It is a complex mixture of several hundreds of different chemical components, some of which include carbohydrates, proteins, amino acids, polypeptides, lipids, polyphenols, organic ions, vitamins, hop components, and other numerous nutrients, minerals, etc.—with the result that identifying real-world opportunities to manage the diacetyl problem is enormously complicated.

Nevertheless, and in accordance with the present invention, diacetyl formation can be reliably dealt with by managing the interrelationship between initial carbohydrate and free amino nitrogen (FAN) concentrations and the specific gravity, of the wort composition. Although the merits of the present invention are in no way dependent upon the veracity of this hypothesis, it is presently believed that during the sequential uptake of type 'B' amino acids, the internal valine concentration becomes high enough that the enzyme AHA synthase is repressed. This reduces the production of α-acetolactate, the flux of the valine biosynthetic pathway and thus diacetyl production. At this point in time, the diacetyl profile now enters its first 'net' reduction phase. As the internal valine is either catabolized or compartmentalized (i.e. contained within intra-cellular structures), the effects are reversed and a derepression of AHA synthase occurs. If under these evolving conditions, sufficient fermentable sugars remain available, and the yeast are healthy and viable, the valine biosynthetic pathway once again proceeds with an increased flux and increased diacetyl production results. This period after derepression is called the second 'net' production phase. If the fermentable sugars have been reduced to a minimum by this time, this second 'net' production phase is less pronounced or non-existent. Often this second peak gets stuck at high levels, with little diacetyl reducing power so late in fermentation. Based on this reasoning, the balance and timing of the fermentative power, supplied by the fermentable sugar content and the valine content which ultimately controls the repression/derepression cycle is critical and, for that reason, is predictable from the outset in accordance with the present invention. It is this interrelationship that is important in the prevention of the exhaustion of key type 'B' amino acids before the fermentable sugar concentration is depleted which prevents the production of diacetyl once again later in fermentation. The present invention is based on the discovery that it is the ratio of these three initial wort characteristics which determines the late fermentation production (e.g. the appearance of the second diacetyl peak) in wort fermentations.

Therefore, in accordance with the present invention there is provided a method for predicting late fermentation production of diacetyl in a brewing process, comprising determining the ratio of FAN (free amino nitrogen content) to sugar (fermentable) to gravity in an initial wort composition. The predictability of late fermentation production of diacetyl formation allows the brewer advance warning that can be useful in scheduling/specifying post-fermentation remediation, or taking proactive measures to avoid the problem altogether. In this later regard, the invention also relates to a process for preventing (deterring, mitigating against or in any case reducing the risk or incidence of) incipient late fermentation production of diacetyl in a brewing process, comprising measuring the initial FAN, sugar and gravity of the wort and calculating the ratio $$\frac{[f.\text{sugar}(g/L)]_{initial}}{[\text{FAN}(g/L)]_{initial}[\text{Gravity}(°P)]_{initial}},$$

($g_{f.sug}$/gFAN/° P) on the basis of those measurements, and then supplementing if and as needed to reduce the value of the ratio to 37 or less.

In accordance with another aspect of the present invention, there is provided a wort composition wherein said ratio $$\frac{[f.\text{sugar}(g/L)]_{initial}}{[\text{FAN}(g/L)]_{initial}[\text{Gravity}(°P)]_{initial}},$$

($g_{f.sug}$/gFAN/° P) is 37 or less, as well as a process for producing such a wort, comprising combining an ingredient constituency to produce a $$\frac{[f.\text{sugar}(g/L)]_{initial}}{[\text{FAN}(g/L)]_{initial}[\text{Gravity}(°P)]_{initial}},$$

($g_{f.sug}$/$g$FAN/° P)ratio of 37 or less to forestall.

In yet another aspect of the present invention, there is provided a brewing process having an abbreviated maturation stage, comprising fermenting a wort having an initial $$\frac{[f.\text{sugar}(g/L)]_{initial}}{[\text{FAN}(g/L)]_{initial}[\text{Gravity}(°P)]_{initial}},$$

($g_{f.sug}$/gFAN/° P) ratio of 37 or less to forestall/prevent late fermentation production of diacetyl. This is related to the underlying method for diverting the biochemical pathways of brewers yeast that lead to the production of diacetyl during fermentation by controlling the initial wort constitution such that the ratio of $$\frac{[f.\text{sugar}(g/L)]_{initial}}{[\text{FAN}(g/L)]_{initial}[\text{Gravity}(°P)]_{initial}},$$

($g_{f.sug}$/gFAN/° P) has a value of 37 or less.

The present invention also finds application as a method for conditioning a yeast cell population to forestall late fermentation production of diacetyl, comprising conditioning said cells through lag phase in a wort having a $$\frac{[f.\text{sugar}(g/L)]_{initial}}{[\text{FAN}(g/L)]_{initial}[\text{Gravity}(°P)]_{initial}},$$

($g_{f.sug}$/gFAN/° P) ratio of 37 or less. This is particularly useful in raising a yeast pitching mass in a wort having a $$\frac{[f.\text{sugar}(g/L)]_{initial}}{[\text{FAN}(g/L)]_{initial}[\text{Gravity}(°P)]_{initial}},$$

($g_{f.sug}$/gFAN/° P) ratio of 37 or less.

In setting quality technical standards, specifications and procedures, the present invention extends to a method for a production specification comprising establishing a "true-to-type" diacetyl specification for a given beer product, then mapping a corresponding wort composition compliance ratio of $$\frac{[f.\text{sugar}(g/L)]_{initial}}{[\text{FAN}(g/L)]_{initial}[\text{Gravity}(°P)]_{initial}},$$

($g_{f.sug}$/$g_{FAN}$/° P) which (for an otherwise defined process specification) targets the desired final diacetyl specification. Typically such a specification will be a range of final diacetyl concentrations corresponding to a range of the ratio value and corresponding ranges of FAN, sugar and gravity. Preferably, the final diacetyl concentration will be a range that covers a statistical clustering of beers all meeting a threshold of subjective taste test approvals to a predetermined level of statistical confidence, and for which a corresponding objective measure of a range of diacetyl concentrations is analytically measured. It is this latter objective measure that is used to map the corresponding predictor ratio values, and in turn, a range of FAN, fermentable sugar and gravity for the initial wort specification.

INTRODUCTION TO THE DRAWINGS

Various aspects of the present invention are depicted in the appended drawings, in which:

FIG. 1: is a schematic representation of the production and reduction of the vicinyl diketone's: diacetyl and 2,3-pentandione; and, FIG. 2: is a schematic representation of the Isoleucine-Valine-Leucine biosynthetic pathway of yeast, (enclosed area represents the portions which takes place in the mitochondria, red=enzymes, green=genes); and, FIG. 3: is a block process diagram outlining wort preparation: 'Maltose Supplemented' versus 'Typical' Wort; and, FIG. 4: is a graphical depiction of the bioreactor diacetyl concentration (μg/L) vs. Time (hrs). Duplicate low sp. gr. 13.54° P (LG1,□), (LG2,■), duplicate medium sp. gr. 17.44° P (MG1,○), (MG2,●); duplicate high sp. gr., 21.34° P (HG1,△), (HG2,▲), during fermentations using supplemented wort.

DETAILED DESCRIPTION OF THE INVENTION

In order to better illustrate the present invention, forty-two different fermentations were carried out and the results compared. These fermentations were carried out in a series of six (three liter capacity) magnetically stirred Belco bioreactors that had been modified for the control of oxygen by featuring: stirring rod with magnetic stir bar and impeller; a gas purge port; a sampling port for positive pressure sampling; a pressure control port equipped with an air lock bunging attachment, and; a septum injection port for needle entry facilitating $O_2$ purging. A high quality precious metal magnetic stir controller was installed inside a wall incubator where the bioreactors were housed. A stainless steel water bath with false floor enabled water circulation under and around each bioreactor.

Biomass scale-up was initiated by inoculating test tubes with 10 ml of industrial plant wort with a pure yeast culture from the Labatt culture collection (S. cerevisiae, LCC#3021). The test tubes were maintained at 21° C. for 24 hrs, and were then transferred to a 500-ml volumetric flask with 190 ml of the same wort. This flask was agitated at 150 rpm and 21° C. for a further 24 hrs. This was followed by a transfer to a 1000 ml flask with 800 ml of the same wort, where it was agitated for a further 24 hrs. Just before the time of inoculation, the contents of each flask were centrifuged at 3500 rpm for 30 minutes at 4° C. The desired mass of cells was weighed, and transferred into each of 6 bioreactors. The yeast inoculation rate employed was approximately $1 \times 10^6$ cells/ml/° Plato. Degree Plato (° P) is a brewery term used to measure the extent of attenuation or fermentation, and is defined as the normalized specific gravity based on the w/w % of a sucrose solution. That is, ° P refers to the percent sucrose solution, which has the same specific gravity as the solution in question.

Fermentations were previously performed, on each specific gravity and type of wort to obtain their saturation/de-saturation values. The Dr. Thiedig Digox oxygen probe, an electrochemical measurement device, was used for this purpose. The saturated and de-saturated values were used to obtain wort mixtures with the desired initial wort dissolved oxygen concentration (1 ppm $O_2$/° Plato) by combining calculated volumes of oxygen saturated and helium de-saturated wort.

Figure 3:
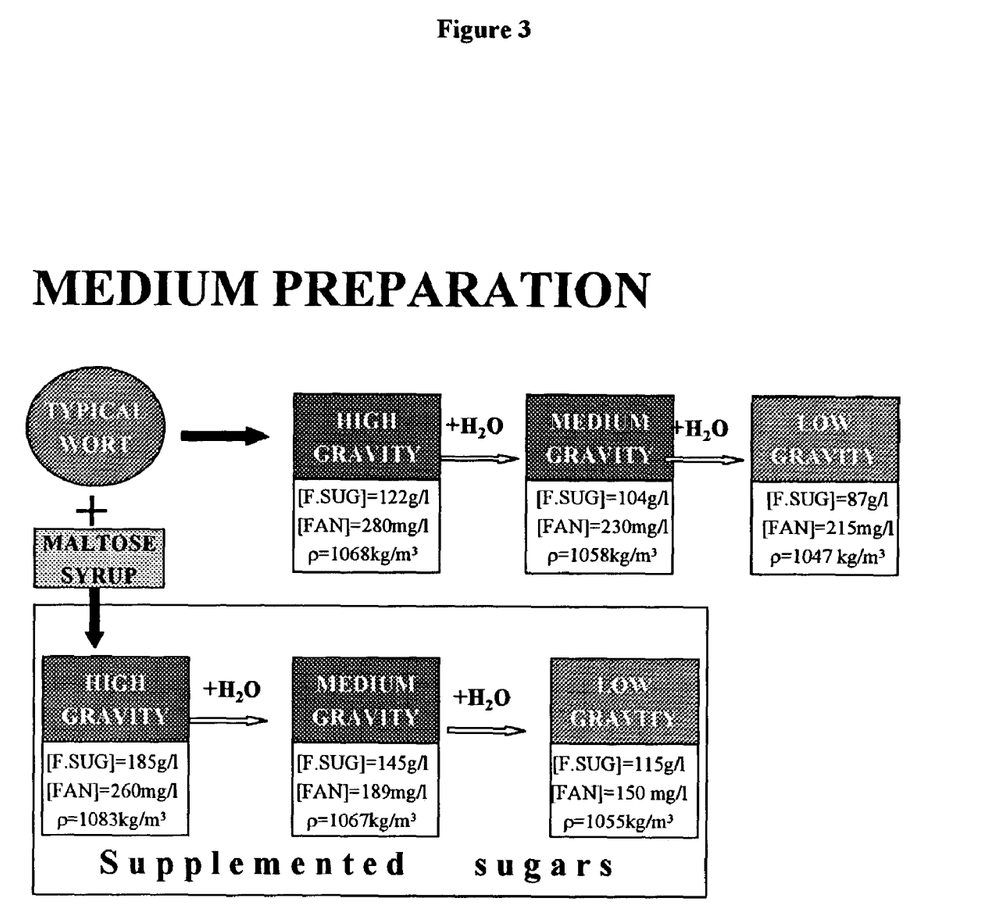

Battery powered temperature data loggers, equipped with microprocessors, data storage and sensors, electronically recorded the temperatures of the bioreactors continuously during fermentations. The results revealed that the introduction of the circulating water bath, provided excellent temperature control. With the incubator set at 15° C., the six bioreactors' temperatures were 15±0.03° C. over a 5 day fermentation. Brewery wort from an industrial supply was collected aseptically, pasteurized and standardized for solids content. Three gravities were produced by diluting a high gravity base wort twice with distilled water. Two base worts were used: 1) typical beer wort, approximately 17° P; and 2) the same typical beer wort supplemented with 75 g/L of maltose syrup, to 20° P. FIG. 3 compares the specific gravities, expressed in density units, fermentable sugar and FAN concentrations of the two wort types, typical and supplemented. Notice that the 'supplemented' wort has a higher fermentable sugar and lower FAN concentration than the 'typical' wort for the same specific gravity. The term fermentable sugars (f.sugars) is defined as the sum of sucrose, fructose, glucose, maltose and maltotriose concentrations. The free amino nitrogen concentration (FAN) is defined as representing the contribution of nitrogen from amino acids, ammonia, and alpha-amino nitrogen groups of peptides and proteins present in the wort. In effect, different ratios of [f.sugars]$_{initial}$/[FAN]$_{initial}$ have been achieved, for varying specific gravities of wort. (Note that FAN supplements are readily available and inexpensive in the brewing arts). All fermentations were performed with the above mentioned protocol in regards to initial cell loading, oxygenation, temperature, stirrer speed, apparatus, and yeast strain, while the wort variations occurred as a result of the different wort carbohydrate and FAN content. Each fermentation involved 6 fermentors, duplicates of the three gravities. Various analyses were performed on each of the 42 fermentations. Samples were taken without introducing oxygen, and in amounts and at frequencies best suited for the analytical requirements throughout fermentation. Biomass dry wt., cell count, viability, pH, and specific gravity were measured, as well as the concentrations of FAN, amino acid, carbohydrates, esters, higher alcohols, acetaldehyde, ethanol, vicinyl diketones, and diols, over the course of fermentation. Beer volatiles such as acetaldehyde, ethyl acetate, isobutanol, 1-propanol, isoamyl acetate, isoamyl alcohol, ethyl hexanoate, and ethyloctanoate, were measured using an internal standard (n-butanol) GC (Hewlett Packard 5890) head space method and flame ionization detector (FID). The specific gravity was measured using a digitalized density meter (Anton Paar DMA-58 Densitometer). Carbohydrate analysis (glucose, fructose, maltose, maltotriose (DP3), maltotetraose (DP4), poly-1(polysaccharide peak 1) and glycerol were measured using a Spectra-Physics (SP8100XR) high performance liquid chromatograph (HPLC) equipped with cation exchange column and a refractive index detector.

Vicinal diketones, diacetyl (2,3-butanedione) and 2,3-pentanedione, were measured using a headspace analyte sampling technique, followed by capillary GC separation (Hewlett-Packard 5890) and electron capture detection (ECD). Total diacetyl was measured (diacetyl and its precursor, alpha acetolactate). Free Amino Nitrogen (FAN) was measured using spectrophotometric method (Perkin Elmer LS50B) which displays and measures a colour reaction between ninhydrin and the nitrogen present in the sample (FAN method ASBC, 1992). Biomass was measured by dry weight analysis, while viability was assessed using methylene blue viability stain. Dissolved oxygen was measured on the Dr. Thiedig Digox 5 dissolved oxygen analyzer, an electrochemical measurement method based on an amperometric three-electrode arrangement with potentiometer. Ethanol was measured using an internal standard gas chromatograph (GC) (Perkin Elmer 8500) equipped with a flame ionization detector (FID) and autosampler. pH was measured by pH meter-Orion model 720A. Temperature was measured by electronic temperature loggers with optical communications.

Forty two fermentations were performed in total, with varying concentrations of fermentable sugars, FAN and specific gravity. Careful planning allowed the isolation of a single variable such that 1) the influences of the controlled variable: (f.sugar/FAN) ratio could be assessed, while keeping constant the carbohydrate composition and specific gravity, and 2) the effects of the controlled variable: specific gravity could be assessed, while keeping constant the (f.sugar/FAN) ratio, and the carbohydrate composition.

Besides the initial valine concentration, a unique ratio exists which also predicted the existence of the double diacetyl peak in all 42 separate fermentations. This ratio, called the predictor ratio (PR), combines the initial fermentable sugar concentration, the initial specific gravity and the initial FAN concentration as follows: Predictor Ratio (PR)= $\{([f.sugar]_{init}/(sp. gr.) [FAN]_{init})\}$, with units of $(g_{F.sugar}/(g_{FAN}.°P))$. From Tables 1.1–1.2 it can be seen that when this ratio is about or less than 37, single diacetyl peaks resulted. This is the ratio of $[f.sugar]_{init}/[FAN]_{init}$ normalized to the specific gravity. This ratio will be discussed later.

Figure 4:
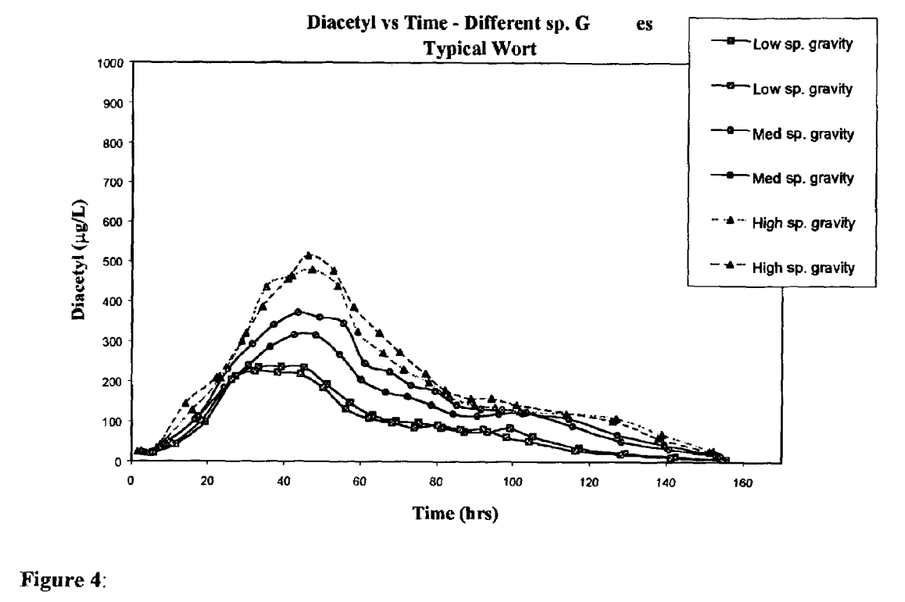
Figure 11:
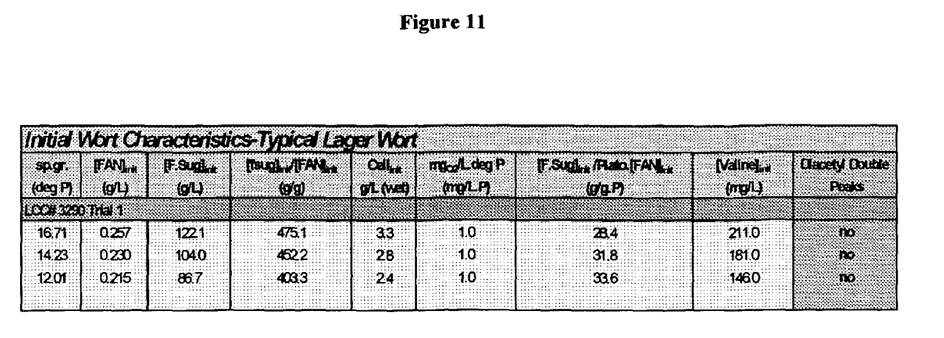
FIG. 11: Initial wort characteristics produced by dilution of typical lager base wort

FIG. 4 illustrates representative diacetyl profiles resulting when the typical worts were fermented. FIG. 11 summarizes the wort characteristics of the typical worts. Consistent with a decrease in specific gravity, the concentration of FAN and fermentable sugars decreased. All fermentations with typical wort resulted in single diacetyl peak profiles, even for the 12.01° P wort. As the specific gravity increased from 12.01 to 16.71° P, there was an increase in the diacetyl concentration maximum, and the net production phase was found to end sooner. Thus, as the initial wort specific gravity increased, the peak position moved further to the right, or later in time. Notice that in both the 12.01° P wort fermentations, there was a delay between the end of the net production phase and the beginning of the net reduction phase, such that there was a plateau which spanned from approximately 25 to 45 hours. Also, as the specific gravity increased, it took longer to reach an end diacetyl level under threshold (45 µg/L) at the end of fermentation. Notice that in the 12.01° P wort, the reduction slowed between 60 and 100 hours, after which it accelerated once again. A similar trend was seen in the 14.23 and 16.71° P worts.

In general, even though the key indicators of fermentation, such as pH, ethanol and biomass production, specific gravity, carbohydrate and FAN consumption varied little and systematically, a variety of unusual diacetyl profiles resulted particularly when fermenting the supplemented wort. Sometimes a later second peak resulted, which will be referred to as the 'double diacetyl peak' phenomenon. In the double diacetyl peak scenario, there are two 'net production' phases, and two 'net reduction' phases. The portion of the plot between the beginning of the first net reduction phase and the beginning of the second net production phases will be referred to as the repression/derepression transition phase, or just simply the transition phase.

Figure 5:
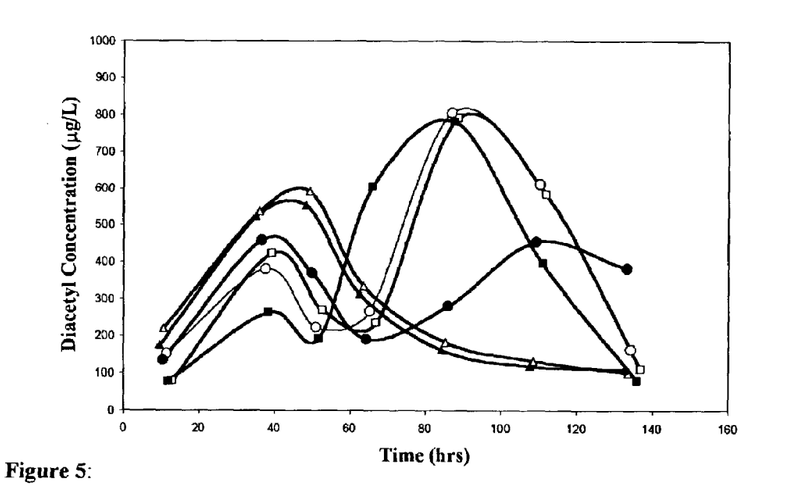
FIG. 5: is a graphical depiction of the bioreactor diacetyl concentration (μg/L) vs. Time (hrs). Duplicate low sp. gr. 12.01° P(□), (■), duplicate medium sp. gr. 14.23° P (○), (●); duplicate high sp. gr., 16.71° P (Δ), (▲), during fermentations using typical wort.
Figure 12:
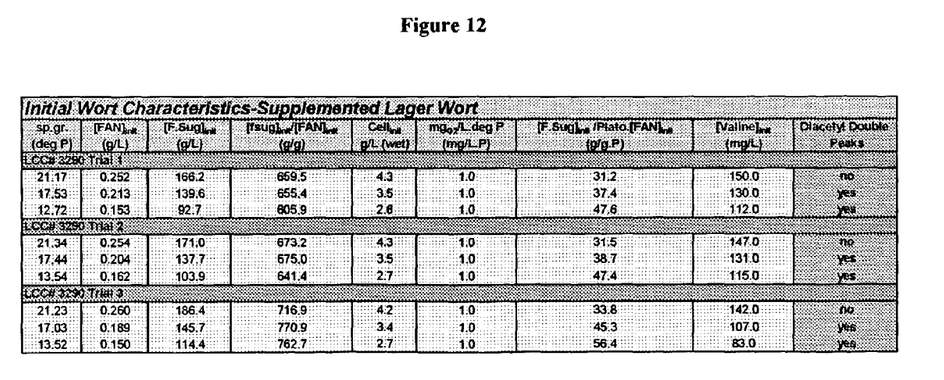
FIG. 12: Initial wort characteristics produced by dilution of maltose supplemented

FIG. 5 illustrates diacetyl profiles resulting when the supplemented worts were fermented. FIG. 12 summarizes the wort characteristics of the maltose supplemented worts. In comparing FIG. 11 and FIG. 12, the supplemented worts have lower FAN and valine concentrations but higher fermentable sugar concentrations, than the typical wort, for the same specific gravity. Thus the supplemented worts had a higher ratio of $[F.sugar]_{init}/[FAN]_{init}$, g/g.

In all three trials, with maltose syrup supplemented wort, double diacetyl peaks resulted with wort in the range of 12.72–17.53° P, but not with wort in the range of 21.17–21.34° P. The double diacetyl peak profiles that resulted were variable in shape with respect to valley and second peak position. Sometimes the first peak 'shouldered' on the side of the second peak, while in other cases, there was a distinct first and second peak, as can be seen in FIG. 5, data in FIG. 12, trial 2. Notice from FIG. 5, that for both duplicate 21.34° P worts, the single diacetyl peak profiles did not reduce below 100 µg/L. In fact, in all three trials, for the specific gravities of 21.17 to 21.34° P, supplemented wort, the diacetyl plots leveled off and maintained a net zero production/reduction at the end of fermentation. Notice from FIG. 5 that, even though duplicate fermentations had the same initial wort conditions, there was divergence of the diacetyl plots in the 13.54 and 17.44° P duplicates. For example, bioreactor LG2, 13.54° P wort, had a low first peak, a short lived transition phase, and a high second peak, while its duplicate, LG1, had a higher first peak, longer transition phase, and similar high second peak. Bioreactor MG1, 17.44° P, began the first reduction phase sooner than MG2, had a shorter transition phase, a higher second peak than MG2, and reduced to an end diacetyl value lower than MG2, and similar to LG1, LG2, HG1, and HG2 by 140 hours. The second diacetyl peaks in the 13.54° P worts, even though they reached high values, reduced to low levels by 140 hours. In general, the second diacetyl peaks in the 16 to 18° P supplemented worts did not always reduce to levels below threshold by the end of fermentation and were very inconsistent. In fact the diacetyl level at 140 hours for MG2, 17.44° P duplicate, was just under 400 µg/L when all others were less than 100 µg/L.

Figure 6:
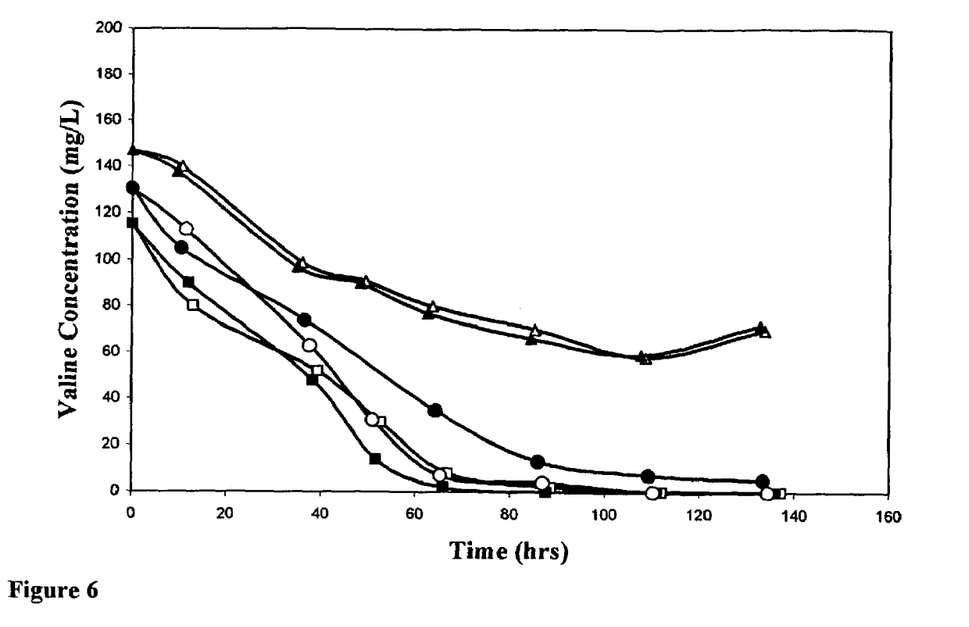
FIG. 6: Bioreactor valine concentration (mg/L) vs. time (hrs) FIG. 12, Trial 2. Duplicate low sp. gr. 13.54° P (LG1,□), (LG2,■), duplicate medium sp. gr. 17.44° P (MG1,○), (MG2,●); duplicate high sp. gr., 21.34° P (HG1, Δ), (HG2,▲), during fermentations using supplemented wort.

FIG. 6, is the plot of valine concentration versus time for the maltose supplemented wort, data in Table 2, Trial 2. For the arbitrary time of 50 hours, it can be seen that the bioreactor valine concentration was the lowest, and approximately 15 mg/L, in LG2, one of the 13.54° P worts. Bioreactors LG1, the other 13.54° P wort and MG1, 17.44° P wort converged and had the next lowest valine concentration, approximately 30 mg/L. Bioreactor MG2, 17.44° P, trailed its duplicate, with a value of approximately 55 mg/L valine concentration at 50 hours. Finally, the results of HG1 and HG2, 21.34° P showed the slowest valine uptake rates, had a value of approximately 95 mg/L at 50 hours and did not ever reach lower than 56 mg/L. In comparing FIG. 5, the diacetyl profile, and FIG. 6, the valine profile, notice that when the valine concentration reaches low levels early in fermentation, as in the case of LG2, the repression/derepression transition time or 'transition phase', is shorter.

Figure 7:
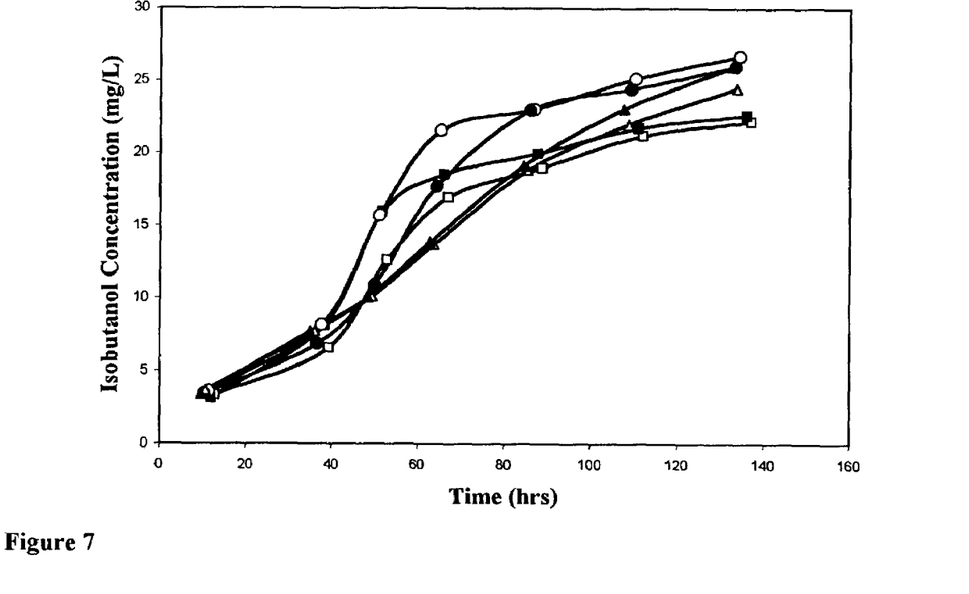
FIG. 7: Bioreactor isobutanol concentration (mg/L) vs. time (hrs), FIG. 12, Trial 2. Duplicate low sp. gr. 13.54° P (LG1,□), (LG2,■), duplicate medium sp. gr. 17.44° P (MG1,○), (MG2,●); duplicate high sp. gr., 21.34° P (HG1, Δ), (HG2,▲), during fermentations using supplemented wort.

In fact, LG2 has the shortest transition phase in diacetyl, followed by LG1 and MG1, both with similar valine depletion and diacetyl transition phase times. Fermenter MG2 finished next in regards to both diacetyl transition phase time and valine depletion, and HG1 and HG2, which never reached 50 mg/L in valine, do not have a transition phase. In general, as the specific gravity decreased, valine depletion occurred sooner, but this general rule did not always apply. The shape of the valine consumption curve and thus the timing of valine depletion appeared to be mostly due to uptake rates and the initial amino acid concentrations, and to a lesser extent, some unknown factors FIG. 7 is the plot of isobutanol concentration versus time for Trial 2, Table 2. Notice that in the 13.54 and 17.44° P wort, at approximately 38 to 42 hours, the isobutanol production accelerated. This point consistently coincided with the time when the first net reduction phase in diacetyl occurred, FIG. 5. For example, LG2, 13.54° P, the fermenter to reach low valine concentrations first and the one with the shortest transition phase in diacetyl, was one of the first bioreactor to show an accelerated rate of isobutanol production. Bioreactor LG1 and MG1, the next to become depleted in valine, FIG. 6, have the next shortest transition phase in diacetyl, FIG. 5, and were the next to show accelerated rates of isobutanol production, FIG. 7. Notice from FIG. 7 that both MG1 and MG2, 17.44° P, had long accelerated isobutanol production phases and produced more isobutanol in the end. In regards to the diacetyl profile these two bioractors, MG1 and MG2 also had the longest diacetyl transition phases, approximately 20 hours. From FIG. 7, notice that LG2, 13.54° P, had one of the lowest ending isobutanol concentrations and was the one with the shortest transition phase, approximately 8 hours.

Analysis revealed that there was no consistent relationship between either of the initial fermentable sugar concentration, FAN concentration, or specific gravity, alone and the presence of a double diacetyl peak. For each fermentation, and from one fermentation to the next, the FAN composition (% individual amino acids) remained constant.

Figure 8:
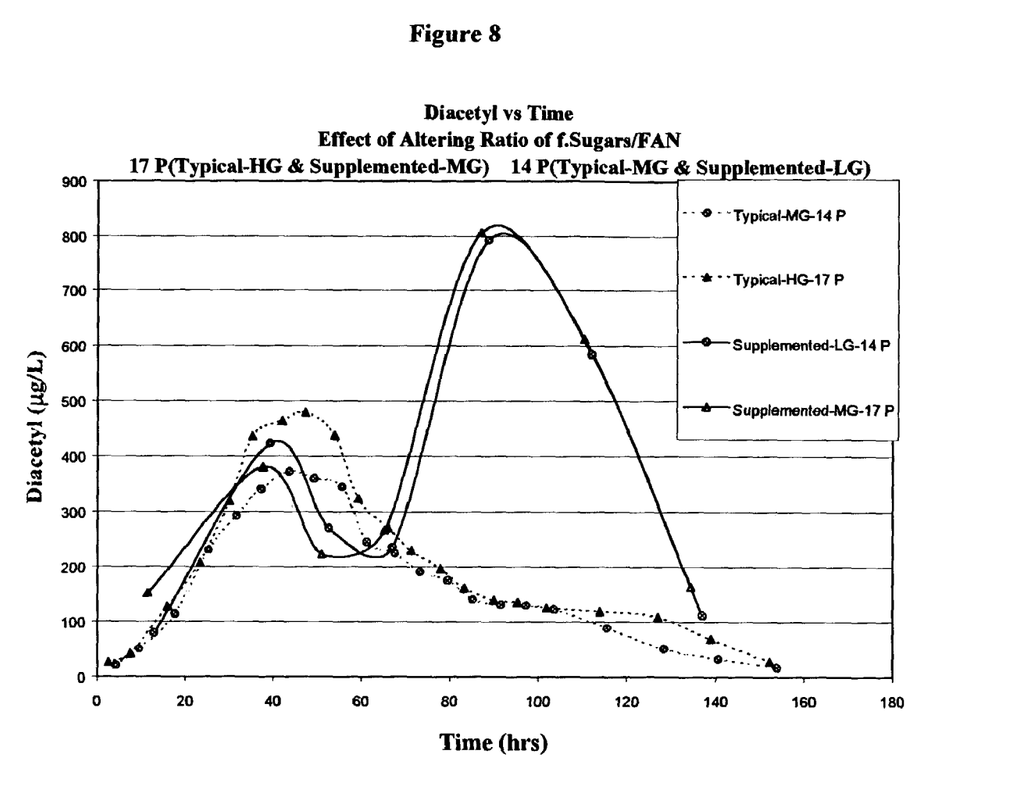
FIG. 8: is a representative plot of the change in diacetyl concentration over time: illustrating the effects of altered initial ratio of fermentable sugars-to-fAN for 14 degree Plato (●), 17 degree plato (▲), High f.sugar/FAN-supplemented wort (______), Low f.sugar/FAN—typical wort ( . . . ).

The effects of the ratio of (f.sugars/FAN) on diacetyl production comparing supplemented to typical wort at two different specific gravities can be best illustrated with FIG. 8. FIG. 8 is a representative plot of diacetyl production for two worts with the same carbohydrate composition and sp. gravity but which vary in the initial ratio of the concentrations of (f.sugar/FAN). The solid lines represents the diacetyl profile for the fermentations using supplemented wort which had a high ratio of (f.sugar/FAN) and the dashed lines represent the diacetyl profile for the fermentations using typical wort which had a low ratio of (f.sugar/FAN). Notice that double diacetyl peaks resulted in the supplemented wort with the high ratio of (f.sugar/FAN). Overall, the fermentations did not show a consistent ratio of (f.sugar-to FAN) value that could predict the presence of double diacetyl peaks.

Further analysis demonstrated the double diacetyl peak could be predicted using fermentable sugar and FAN concentrations and specific gravity, of the initial wort. The value of this novel ratio, $$\frac{[F.\text{sugar}(g/L)]_{initial}}{[FAN(g/L)]_{initial}[\text{Gravity}(°P)]_{initial}},$$

($g_{f.sug}/g_{FAN}/°$ P) which is defined as the concentration of fermentable sugars divided by the product of the concentration of FAN and the specific gravity of the initial wort, correlated with the occurrence of double diacetyl peaks is seen in Tables 1.1 and 1.2.

Figure 9:
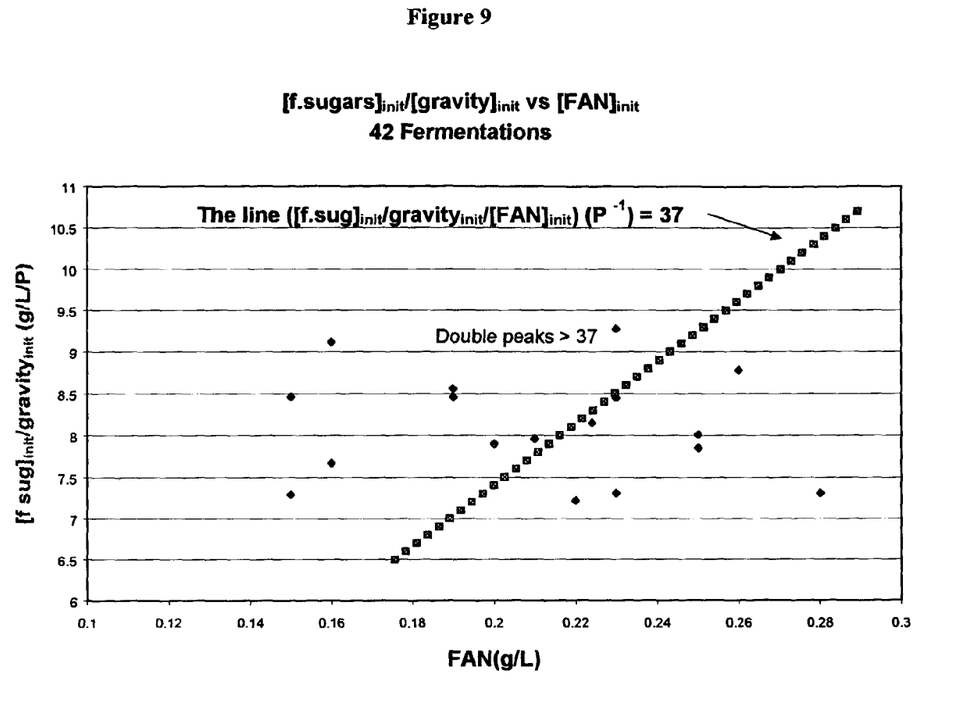
FIG. 9: Illustrates the value of the predictor ratio of 37 as an overlay on a plot of the respective ([f.sugar]$_{init}$/specific gravity) (g/L° P) vs [FAN]$_{init}$ (g/L) for all 42 fermentations.

The plot of ([f sugar]$_{init}$/specific gravity$_{init}$) (g/L° P) vs [FAN]$_{init}$ (g/L) is shown in FIG. 9. The solid line indicates where the values of the x and y axis renders a ratio of value 37 ($g_{f.sug}/g_{FAN}/°$ P), which marks the line between the initial conditions that cause a single diacetyl peak and those which result in a double diacetyl peak. The actual fermentation values are shown with diamonds. Al points which have values below the line, exhibited single diacetyl peaks, and those above, exhibited double diacetyl peaks.

Figure 10:
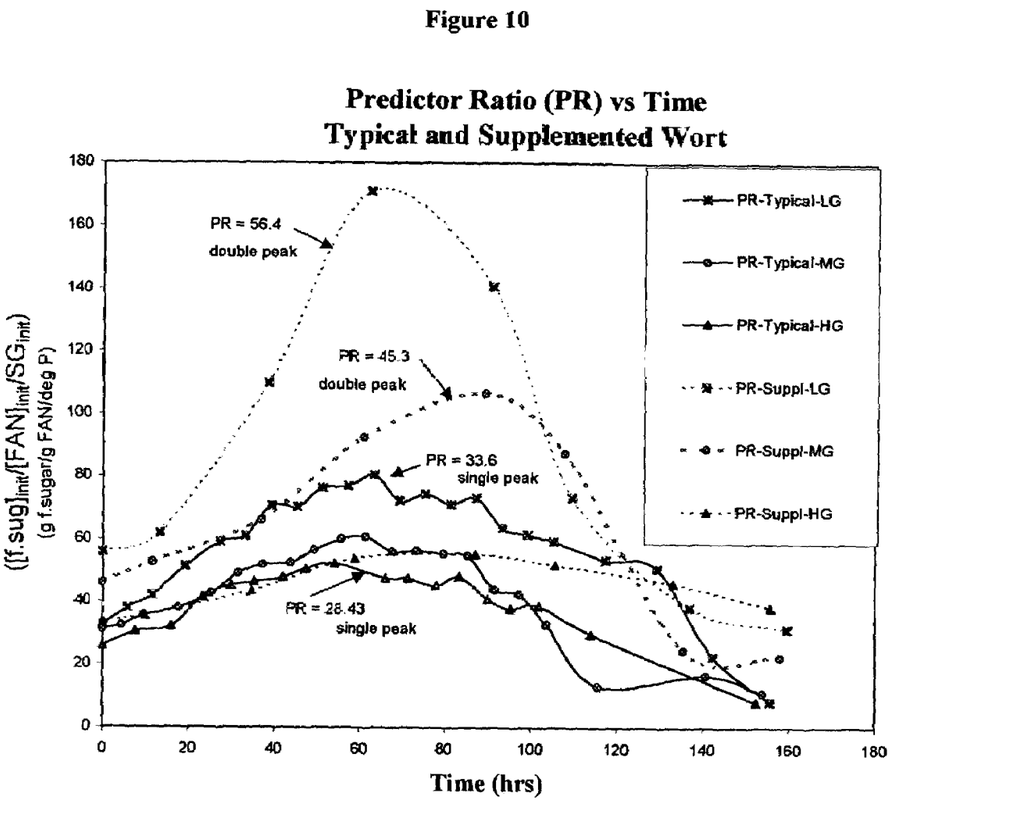
FIG. 10: Illustrates changes in the ratio ([f.sugar]$_{init}$/specific gravity)/[FAN]$_{init}$ (g f.sug/g FAN/° P) vs. Fermentation Time (hrs) for typical and supplemented worts, as follows: Low sp. gravity (■), Med sp. gravity (●), High sp. gravity (▲), Typical wort (______), and Supplemented wort ( . . . ).

There was evidence that there was a relationship between the shape of the plot of the same ratio ([f.sugar]/specific gravity)/[FAN]($g_{f.sug}/g_{FAN}/°$ P) evaluated at different times during fermentation and the diacetyl profile. This ratio, when evaluated over time is plotted in FIG. 10, where the solid lines representing the ratio when using typical wort, and the dashed lines represent the ratio over time using supplemented wort. When the PR ratio, evaluated on initial conditions, is high, the ratio evaluated over time produces a high peaked plot, whereas when the ratio evaluated on initial conditions, is low, the ratio evaluated over time, produces a low flat plot. The significance of the plot of the predictor ratio over time illustrates the influence of an imbalance in the rate of FAN uptake and fermentable sugar uptake, such that when the plot is a high peak, imbalance exists. This ratio, when evaluated at different times during fermentation, instead of initial conditions, and plotted over the course of fermentation, also offered insight as to its significance. The plot of this ratio over time is a reflection of the balance in the rates of uptake in fermentable sugars and FAN. The peak indicates a point when the rate of FAN uptake subsides and the rate of fermentable sugar predominates. The taller peak representing a greater initial FAN uptake, relative to the fermentable sugar uptake, and/or residual fermentable sugars left when there is no FAN left. From FIG. 10 it can be seen that as the gravity was increased, irrespective of the wort type, the magnitude of the PR vs. time profile peak decreased. Thus there appeared to be an optimum ratio of (f.sugar/FAN) for a specific gravity wort.

Diacetyl is a persistent problem in the brewing industry and its evolution has been poorly understood. Furthermore, present methods to reduce diacetyl either involve yeast genetic manipulation or the use of expensive supplementation of specific amino acids or enzymes. A preferred method would be to use biochemical principles to alter the wort composition. The fermentations performed have shown that the ratio of ([f.sugar]$_{init}$/specific gravity)/[FAN]$_{init}$ ($g_{f.sug}/g_{FAN}/°$ P) determined the presence of a double peak. When the value of this ratio was less than 37 ($g_{f.sug}/g_{FAN}/°$ P) a single peak occurred. Further, it was found that for a certain initial fermentable carbohydrate concentration and gravity combination, there was a required minimum FAN concentration that would ensure a single peak in diacetyl and thus quicker maturation. This relationship was illustrated in FIG. 9 and its concept is discussed further.

As [f.sugar]$_{initial}$ increases, the ratio increases which, by the claim in this report, increases the risk of a double diacetyl peaks forming. This can be explained by the fact that as the fermentable sugar concentration increases, the rate of fermentation or fermentative power increases such that there is increased growth which is sustained for longer periods of time. As [FAN]$_{initial}$ increases, on the other hand, there is less risk of a double peak forming, as there is less risk of using up or exhausting type B amino acids. When the total FAN increases, so does valine, and if there is enough valine, the critical valine concentration which initiates the derepression and second net production phase will never be reached. As the total FAN decreases, so does valine, and the initiation of derepression may occur. The role of gravity as a factor is unobvious in relation to the previous two factors. A wort can have a high ratio of (f.sug$_{init}$/gravity$_{init}$), (g$_{f.sugar}$/° P) and be low in FAN, as in the case of syrup supplementation, but a wort with a low ratio of (f.sug$_{init}$/gravity$_{init}$), (g$_{f.sugar}$/° P) without a high FAN concentration is unlikely. Thus, the ratio of (f.sug$_{init}$/gravity$_{init}$), (g$_{f.sugar}$/° P) is believed to be a measure of the dilution factor. This unique ratio, therefore, represents the ratio of fermentable sugars to FAN, normalized to specific gravity. This means that the balance between fermentable carbohydrates and valine is important but becomes predictive only in relation to the initial specific gravity of the wort.

When valine and fermentable sugar concentrates are both low, second peaks may result, but they tend to occur earlier during fermentation, and the resulting diacetyl tends to be reduced to low levels before the end of fermentation. The PR ratio is most relevent as a predictor of high late fermentation diacetyl levels, in situations where the combination of medium levels of valine (the transition phase was prolonged with the result that the second net production phase occurred later in fermentation) and high fermentable sugar levels.

The ability of the predictor ratio to be successful, indicates that the double/single diacetyl peak scenario can be determined on the basis of initial wort composition. In other words double diacetyl peaks can occur in the stationary phase, and appear to be caused by a combination of the enzymatic regulation of amino acid biosynthesis, more specifically valine uptake behavior, and the fermentative power supplied by the carbohydrate resource and is not necessarily directly related to growth. It should be mentioned that what makes this predictability possible is the consistency in the sequential, behavior of the amino acid uptake and the constant percent by mass of valine of the total amino acid content, a property of the malt protein. What would make the sequential uptake possible is an amino acid transport system that is regulated by external environmental amino acid concentrations in some way.

Applications for such a predictor ratio could be in the prevention of high diacetyl levels in the finished beer, by properly designing the wort composition to reflect 'safe' ratios, or in the case of correcting worts already prepared with unbalanced ratios before fermentation begins. Other aspects of the present invention will be readily apparent to persons skilled in the art in light of the present invention.

What is claimed is:

1. A process for preventing incipient late fermentation production of diacetyl in a brewing process, comprising measuring the initial wort FAN and fermentable sugar concentrations and the specific gravity of a wort composition and then calculating the ratio $$\frac{[F \cdot \text{sugar (g/L)}]_{initial}}{[FAN \text{ (g/L)}]_{initial}[\text{Gravity}(° P)]_{initial}}$$

and then altering one of more of the FAN and fermentable sugar concentrations and specific gravity of the wort composition, as needed, to reduce said ratio to about 37 or less, prior to fermentation of the wort composition.

2. A method for producing a wort, comprising combining components in a wort composition in predetermined quantities to produce a wort composition having a $$\frac{[F \cdot \text{sugar (g/L)}]_{initial}}{[FAN \text{ (g/L)}]_{initial}[\text{Gravity}(° P)]_{initial}}$$

ratio of about 37 or less.

3. A brewing process having an abbreviated maturation stage, comprising fermenting a wort composition having a $$[\text{F.sugar(g/L)}]_{initial}/[\text{FAN(g/L)}]_{initial}[\text{Gravity}(° P)]_{initial}$$

ratio of about 37 or less to forestall/prevent late fermentation production of diacetyl.

4. A method of diverting biochemical pathways of brewer's yeast that lead to the production of diacetyl during late fermentation of a wort composition comprising controlling the wort composition such that the ratio of $$\frac{[F \cdot \text{sugar (g/L)}]_{initial}}{[FAN \text{ (g/L)}]_{initial}[\text{Gravity}(° P)]_{initial}}$$

has a value of about 37 or less.

5. A method of conditioning a yeast cell population to forestall late fermentation production of diacetyl, comprising conditioning the yeast cells in the yeast cell population through lag phase in a wort composition having a $$\frac{[F \cdot \text{sugar (g/L)}]_{initial}}{[FAN \text{ (g/L)}]_{initial}[\text{Gravity}(° P)]_{initial}}$$

ratio of about 37 or less.

* * * * *